(12) United States Patent
Olson

(10) Patent No.: US 8,071,799 B2
(45) Date of Patent: Dec. 6, 2011

(54) CHAIN-SELECTIVE SYNTHESIS OF FUEL COMPONENTS AND CHEMICAL FEEDSTOCKS

(75) Inventor: Edwin S. Olson, Grand Forks, ND (US)

(73) Assignee: Energy & Environmental Research Center Foundation, Grand Forks, ND (US)

( * ) Notice: Subject to any disclaimer, the term of this patent is extended or adjusted under 35 U.S.C. 154(b) by 174 days.

(21) Appl. No.: 12/361,748

(22) Filed: Jan. 29, 2009

(65) Prior Publication Data

US 2010/0191008 A1    Jul. 29, 2010

(51) Int. Cl.
  C11C 3/00    (2006.01)
  C11C 3/10    (2006.01)

(52) U.S. Cl. ........ 554/163; 554/162; 554/170; 562/590; 562/595

(58) Field of Classification Search .......................... None
See application file for complete search history.

(56) References Cited

U.S. PATENT DOCUMENTS

| | | | |
|---|---|---|---|
| 3,524,896 A * | 8/1970 | Wu et al. ...................... | 585/509 |
| 4,511,747 A * | 4/1985 | Wright et al. ................. | 585/415 |
| 4,545,941 A | 10/1985 | Rosenburg | |
| 7,119,216 B2 * | 10/2006 | Newman et al. .............. | 554/163 |
| 2007/0270621 A1 | 11/2007 | Millis et al. | |

FOREIGN PATENT DOCUMENTS

| KR | 1020030086323 A | 11/2003 |
|---|---|---|
| WO | WO-2010123589 A2 | 10/2010 |

OTHER PUBLICATIONS

Ngo, H. L., et al., Synthesis of long chain unsaturated-alpha, omega-dicarboxylic acids from renewable materials via olefin metathesis, 2007, J. American Oil Chemists' Society, vol. 84, pp. 777-784.*
Sridhar, R., et al., Modificaitn of selected edible vegetable oils to high oleic oils by lipase-catalyzed ester interchange, 1991, J. Agri. Food Chem., vol. 39, No. 11, pp. 2069-2071.*
Boelhouwer, C and Mol, J. C. "Metathesis of Fatty Acids Esters," Journal of the American Oil Chemists Society, dated Feb. 1984, vol. 61 No. 2 (pp. 425-430).
International Search Report, International Application No. PCT/US2010/020357, dated Nov. 9, 2010, 7 pages.

* cited by examiner

*Primary Examiner* — Porfirio Nazario Gonzalez
*Assistant Examiner* — Yate K Cutliff
(74) *Attorney, Agent, or Firm* — Schwegman, Lundberg & Woessner, P.A.

(57) ABSTRACT

A method comprising providing a starting composition comprising a polyunsaturated fatty acid, a polyunsaturated fatty ester, a carboxylate salt of a polyunsaturated fatty acid, a polyunsaturated triglyceride, or a mixture thereof; self-metathesizing the starting composition or cross-metathesizing the starting composition with at least one short-chain olefin in the presence of a metathesis catalyst to form self-/cross-metathesis products comprising: cyclohexadiene; at least one olefin; and one or more acid-, ester-, or salt-functionalized alkene; and reacting cyclohexadiene to produce at least one cycloalkane or cycloalkane derivatives. A method for producing cycloalkanes for jet fuel by providing a starting composition comprising at least one selected from the group consisting of algal and polyunsaturated vegetable oils, subjecting the starting composition to metathesis to produce metathesis product comprising at least one olefin, cyclohexadiene, and at least one acid-, ester-, or salt-functionalized alkene, and reacting the at least one olefin and cyclohexadiene to form cycloalkane(s).

6 Claims, 7 Drawing Sheets

CHAIN-SELECTIVE SYNTHESIS OF FUEL COMPONENTS AND CHEMICAL FEEDSTOCKS

STATEMENT REGARDING FEDERALLY SPONSORED RESEARCH OR DEVELOPMENT

This invention was made with U.S. government support under Contract No. W911NF-07-C-0046 awarded by the Defense Advanced Research Projects Agency (DARPA). The government has certain rights in this invention.

CROSS-REFERENCE TO RELATED APPLICATIONS

Not applicable.

BACKGROUND OF THE INVENTION

1. Field of the Invention

The present invention relates generally to the production of fuel blendstocks and chemical products. More specifically, the present invention relates to a process for the simultaneous production of chemical feedstocks and fuel blendstocks such as jet fuel from unsaturated and polyunsaturated vegetable oils and/or algal oils. Still more specifically, the present invention relates to a process for the simultaneous production of chemical feedstocks and fuel blendstocks in the absence of thermal or catalytic cracking of carbon chains into numerous small fragments and/or without reduction of ester moieties.

2. Background of the Invention

The ability to exchange alkylidene units of unsaturated vegetable oils presents unique opportunities for synthesis of desirable-chain-length compositions. The exchange reaction employed is known as olefin metathesis. Olefin metathesis can be catalyzed by a variety of transition metal compounds that can form a carbene intermediate with the alkylidene fragment. A description of olefin metathesis may be found in the text *Olefin Metathesis* by K. J. Ivin (Academic Press, New York, 1983).

The cross-metathesis of unsaturated fatty esters with alpha-olefins has been known for some time. As described by E. Verkuijlen et al. (Recl. Tray. Chim. Pays-Bas 1977, 96(8), M86-M90), co-metathesis of methyl oleate and 3-hexene gives 3-dodecene and methyl 9-dodecenoate. Recent patent applications address the use of the unsaturated ester portion of the metathesis products of vegetable oils. For example, in U.S. Patent Application 2005/0154221 A1, Lysenko et al. disclose conversion of short monounsaturated ester product to an aldehyde ester and subsequently to amino esters or hydroxyl esters, which are useful polymer intermediates. In PCT Application PCT/US2007/021931, Abraham et al. disclose conversion of the unsaturated ester to an amino ester.

A disadvantage of conventional metathesis processes is that the feedstock is generally converted into a product with limited usefulness. Accordingly, there is a need in the art for methods integrating cross-metathesis and/or self-metathesis with processing whereby cyclic difunctional monomers useful for the synthesis of polyurethane, polyamide, and other valuable polymers can be produced, as well as desired distributions of alkenes and unsaturated fatty esters that can be converted to desired fuel components. In applications, the method provides for conversion of substantially all of a biomass feedstock to high-value fuel blendstock components and chemical intermediaries.

BRIEF SUMMARY

Herein disclosed is a method comprising: providing a starting composition comprising a polyunsaturated fatty acid, a polyunsaturated fatty ester, a carboxylate salt of a polyunsaturated fatty acid, a polyunsaturated triglyceride, or a mixture thereof; self-metathesizing the starting composition or cross-metathesizing the starting composition with at least one short-chain olefin in the presence of a metathesis catalyst to form metathesis products comprising: cyclohexadiene; one or more olefin compounds; and one or more acid-, ester-, or salt-functionalized alkene comprising at least one carbon-carbon double bond; and reacting at least a portion of the cyclohexadiene to produce at least one selected from the group consisting of cycloalkanes and cycloalkane derivatives. In embodiments, at least a portion of the cycloalkanes are used for fuel blendstock. In applications, reacting the at least a portion of the cyclohexadiene comprises catalytically reacting at least a portion of the cyclohexadiene to produce disubstituted or di-functionalized cyclohexane derivatives.

The disubstituted or di-functionalized cyclohexane derivatives may have the formula $C_6H_{10}X_2$, where X is selected from the group consisting of CN, CHO, and $CH_2NH_2$. In embodiments, the disubstituted or di-functionalized cyclohexane derivatives are cyclohexanedicarboxaldehyde derivatives having the formula $C_6H_{10}(CHO)_2$. The method may further comprise reducing the carboxaldehyde groups to form alcohol groups.

In applications, the disubstituted or di-functionalized cyclohexane derivatives are dinitrile derivatives having the formula $C_6H_{10}(CN)_2$. The method may further comprise hydrolyzing the nitrile groups to form carboxylic acid groups. The method may further comprise hydrogenating the nitrile groups to form amine groups.

In applications, the cycloalkane derivatives comprise alkylcyclohexane derivatives having the formula $C_6H_{11}R$, where R is selected from alkyl groups. Reacting the at least a portion of the cyclohexadiene may comprise reacting cyclohexadiene with a feed comprising olefins. In embodiments, at least a portion of the olefins in the feed comprising olefins were produced via the metathesis reaction.

In applications, the method further comprises converting at least one of the metathesis products to produce at least one fuel blendstock component selected from alkanes, isoalkanes, and cycloalkanes. In applications, the at least one fuel blendstock has a chain length in the range of from eight to fourteen carbon atoms. The fuel blendstock may be suitable for use in at least one selected from the group consisting of JP-4, JP-5, JP-8, Jet A, and Jet A1 fuels. In applications, the fuel blendstock is tailored by limiting the metathesis reaction by adjusting at least one selected from the reaction temperature, reaction time, amount of catalyst, and amount of co-reactant olefin, whereby a desired comprehensive distribution of chain lengths is obtained from partial completion of the metathesis reaction.

In embodiments, the method further comprises converting at least a portion of the metathesis products to azeleic acid. The starting composition may comprise vegetable oil. The starting composition may comprise algal oil.

In embodiments, the one or more olefin metathesis product comprises light olefins selected from 1-propene and 1-butene, and the method further comprises oligomerizing the light olefin product to produce kerosene fuel components having chain lengths in the range of from about eight to sixteen carbons. In applications, oligomerizing comprises treatment with strong acid.

In applications, the method comprises cross-metathesis of a starting composition comprising algal oil, and the at least one short chain olefin comprises ethylene. In embodiments, the at least one short chain olefin consists essentially of ethylene. In applications, the method comprises cross-metathesis of a starting composition comprising omega-unsaturated vegetable oil containing linolenic acid. The vegetable oil may be selected from the group consisting of flaxseed, rapeseed, camelina, soy, and palm oils.

In applications, the starting composition comprises algal oil, and the metathesis product comprises one or more olefin compound determined by the selection of the at least one short chain olefin co-reactant, an unsaturated carboxylic acid or ester with five or more carbons and unsaturation at C-4, and a saturated ester fraction. The method may further comprise processing the saturated ester fraction via selective lipase reaction. In embodiments, selective lipase reaction comprises lipase-catalyzed interesterification of an acyl portion of the saturated ester fraction with canola oil, and interesterification produces a low-melting point modified triglyceride comprising saturated and monounsaturated fatty acids and having a melting point in the range of from about 90° F. to about 100° F. In applications, the method further comprises producing a heat-absorbing material from the low-melting point modified triglyceride. The heat-absorbing material may comprise a panel that is capable of absorbing external or internal heat, when in close contact with human skin, maintaining the skin at normal skin temperature.

Also disclosed herein is a method of producing at least one fuel or fuel component and at least one chemical product from a starting composition comprising a polyunsaturated fatty acid, a polyunsaturated fatty ester, a carboxylate salt of a polyunsaturated fatty acid, a polyunsaturated triglyceride, or a mixture thereof, the method comprising: self-metathesizing the starting composition or cross-metathesizing the starting composition with at least one short-chain olefin in the presence of a metathesis catalyst to form metathesis products comprising: cyclohexadiene; one or more olefin compounds; and one or more acid-, ester-, or salt-functionalized alkene comprising at least one carbon-carbon double bond; utilizing a first portion of the metathesis products to produce a fuel blendstock; and utilizing a second portion of the metathesis products to produce a chemical product. In embodiments, the chemical product is selected from difunctional cyclohexane derivatives and disaturated acyl mono-oleyl glycerides having melting points of less than 100° F.

Thus, embodiments described herein comprise a combination of features and advantages intended to address various shortcomings associated with certain prior processes. The various characteristics described above, as well as other features, will be readily apparent to those skilled in the art upon reading the following detailed description and by referring to the accompanying drawings.

BRIEF DESCRIPTION OF THE DRAWINGS

For a detailed description of the preferred embodiments of the invention, reference will now be made to the accompanying drawings in which.

In the figures, like numerals are used to refer to like steps, for example, 100-series numerals (e.g., 100, 101, 102, etc.) refer to metathesis steps, 200-series numerals (e.g., 200, 201, 202, etc.) refer to downstream processing steps, 300-series numerals (e.g., 300, 301, 302, etc.) refer to separation steps, 400-series numerals (e.g., 400, 401, 402, etc.) refer to fuel production downstream processing steps, 500-series numerals (e.g., 500, 501, 502, etc.) refer to chemical production downstream processing steps, and so on. In instances, a step labeled with a fuel processing or 400-series numeral may be suitable as a chemical production or 500-series step as well, and vice versa.

NOTATION AND NOMENCLATURE

The term "spec fuel" as used herein refers to fuel described by national or international standards wherein the density, boiling range, freezing point, flash point, aromatic content, and/or other specifications are satisfied by testing procedures.

The term "R group" as used herein refers to methyl or triglyceryl groups. The term "R' group" refers to hydrogen, or alkyl groups having from 1 to 12 carbons; desirably, R' groups are selected from hydrogen, methyl, ethyl, and propyl groups. Similarly, "R" groups" refer to alkyl groups having from 1 to 12 carbon atoms, or hydrogen.

DETAILED DESCRIPTION

Overview. Herein disclosed is a process whereby a mixture of valuable chemical intermediates is produced along with fuel product(s) that can be tailored to meet desired fuel specifications. For example, the fuel product may be tailored to meet jet fuel specification JP-8.

The present invention describes methods for the integration of metathesis (cross-metathesis and/or self-metathesis) reaction(s) with processing for formation of alkenes, cyclohexadiene, and unsaturated fatty esters, acids, or salt-functionalized alkenes that can be used to produce fuel components and can also be used to produce desirable chemical feedstocks. For example, the disclosed process can be used to produce cyclic difunctional monomers useful for synthesis of polyurethane, polyamide, and other valuable polymers, and/or a desired distribution of alkenes and unsaturated fatty esters, that can be converted to desirable distributions of specific fuel components. The fuel components can be used to prepare, for example, diesel fuel blendstocks and/or jet fuel. The disclosed integration of metathesis and subsequent downstream processing of metathesis products may provide substantially complete (i.e. approaching one hundred percent) use of a starting composition (also referred to as a feedstock).

Figure 1:
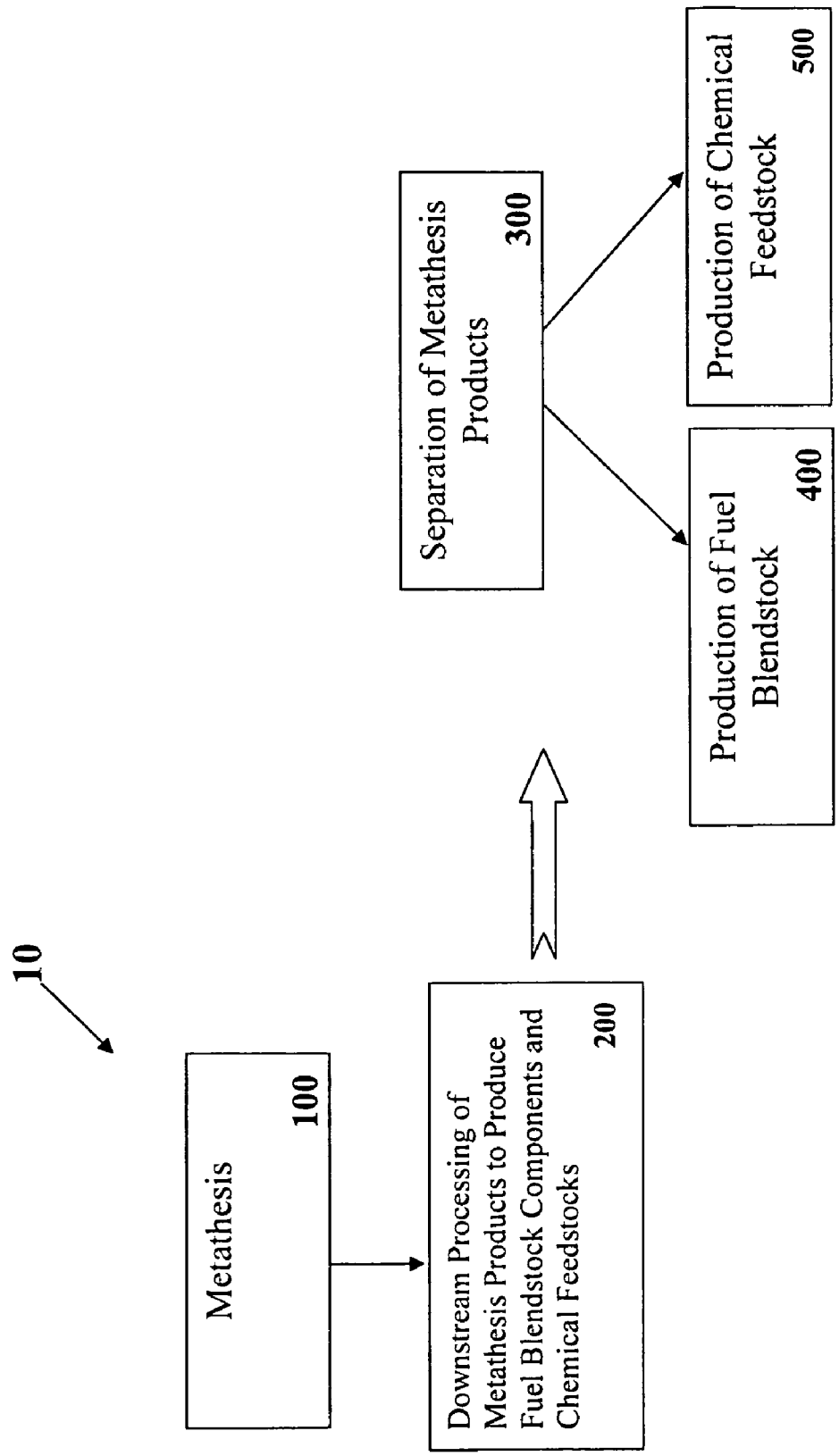
FIG. 1 is a flow diagram of an integrated fuel production and chemical production process according to this disclosure.

FIG. 1 is a flow diagram of an integrated fuel production and chemical production process 10 for the production of chemical feedstocks and fuel blendstocks according to this disclosure. Process 10 comprises metathesis at block 100 and downstream processing at block 200. At block 100, metathesis is used to convert a starting composition into metathesis product comprising cyclohexadiene; one or more olefin compounds; and one or more acid-, ester-, or salt-functionalized alkene comprising at least one carbon-carbon double bond. At block 200, metathesis products are processed to provide at least one chemical feedstock, at least one fuel blendstock component, or, desirably, both. As indicated in the flow diagram of FIG. 1, downstream processing at block 200 comprises separation of metathesis products 300, production of fuel blendstock at block 400 from a first portion of the separated metathesis products, and production of chemical feedstock at block 500 from a second portion of the separated metathesis products.

In embodiments, the present invention is directed to a process for the production, from unsaturated and/or polyunsaturated oils (e.g., vegetable oils), of both fuel blendstocks (including, without limitation, biodiesel fuel, and/or jet fuel), and polymer intermediates (i.e. components utilized to produce polymers) without necessitating cracking into smaller fragments and/or without reduction of the ester moiety.

The key to successfully processing a starting composition, e.g. a triglyceride vegetable oil containing mainly C18 fatty esters, and/or other triglycerides, such as crambe oil or algal oils containing C14 to C22 fatty esters, to fuels and chemicals with desirable combustion and physical properties is to generate the appropriate range of molecule sizes in a target molecular composition. The fuel and chemical production method of this disclosure provides for production of such fuels and chemicals by reformation of C14 to C22 chains according to the placement of the unsaturated bonds in the fatty acid chains of the starting composition.

In the present invention, metathesis reactions are integrated with other processes such that suitable-chain-length fuel components and chemicals are produced. Metathesis at stage 100 causes interchange of pairs of chain units between fatty acid esters of vegetable and/or algal oils or between oil components and suitable olefins. The metathesis products of metathesis stage 100 are processed in the second stage, downstream processing 200, to provide a variety of fuel and chemical products. Downstream processing steps include, without limitation, one or more of separation of metathesis products, hydrogenation of unsaturated products, recombination of selected initial metathesis products via alkylation reactions, isomerization reactions, and additional separation steps.

The types of oils and acids suitable for use in a starting composition treated by the disclosed method contain unsaturated and polyunsaturated fatty acids that exist in various proportions along with saturated fatty acids in vegetable oils. Examples of such useful oils and acids, and a description of the major constituents thereof, are presented in Table 1 below.

TABLE 1

Oils and Acids Suitable for Use in Starting Composition

| Component | Description of Major Constituent(s) |
|---|---|
| Oleic Acid | C18 monounsaturated fatty acid (C18:1) Δ9 |
| Linoleic Acid | C18 diunsaturated fatty acid (C18:2) Δ9, 12 |
| Linolenic Acid | C18 triunsaturated fatty acid (C18:3) Δ9, 12, 15 |
| Vegetable Oil | Unsaturated glycerides of C18:1Δ9, C18:2, Δ9 and 12 and C18:3 fatty acids Δ9, 12, 15 |
| Tung Oil | Unsaturated glycerides of C18:1, C18:2, C18:3 fatty acids |
| Meadowfoam Oil | Unsaturated glycerides of C20:1 fatty acids Δ5 |
| Coriander Oil | Unsaturated glycerides of C15:1 fatty acids Δ6 |
| Camelina Oil | Unsaturated glycerides of C18:3 fatty acids Δ9, 12, 15 |
| Jatropha Oil | Unsaturated glycerides of C18:, C18:2 fatty acids |
| Crambe Oil or High Erucic Rapeseed Oil | Unsaturated glycerides of C22:1 fatty acids Δ13 |
| Algal Oil | Polyunsaturated glycerides of C22:6Δ4, 7, 10, 13, 16, 19 or of C20:5Δ5, 8, 11, 14, 17 fatty acids, plus saturated and unsaturated C14 to C18 fatty acids |

Di- and polyunsaturated components of the starting composition produce the 1,4-cyclohexadiene during metathesis stage 100. Jatropha oils may be especially appropriate, owing to large amounts of polyunsaturation and the ability to grow in poor soils and poor conditions, where they do not compete for acreage with edible vegetable oils. Algal oils are also most useful substrates of a starting composition according to this disclosure, since algal oils typically contain polyunsaturated docosahexaenoic acid (C22:6) along with other acids. The relative amounts of polyunsaturated acids in the starting oil can vary with genetic factors as well as in response to growth conditions. The content of the starting composition can thus be manipulated to some degree to provide products having a desirable chain length and a desirable amount of cyclohexadiene via metathesis at block 100.

Algal oil metathesis processing presents a unique opportunity for preparation of not only cyclohexadiene but also by-products useful for the preparation of low melting fats, such as cocoa butter and shortening and margarine comprising 0-trans fats. The algal oils comprise not only triglycerides (40%-80%) but also large amounts of galactolipids and phospholipids as well as phenolic antioxidants, hydrocarbons, terpenoids, and chlorophyll. Owing to the complex lipid mixtures found in whole algae oil, it is advantageous, in applications, to produce methyl esters from the variety of galactolipids, phospholipids, and triglycerides present. These fatty acid methyl esters (FAMEs) typically contain polyunsaturated fatty acid methyl esters (PUFA MEs) as well as large amounts of saturated esters, such as ME C14 and ME C16 which cannot be easily separated, owing to the instability of the PUFA MEs and the complexity of the lipid content. Cross-metathesis of FAME mixtures with ethylene, according to an embodiment of this disclosure, provides conversion of FAMEs to short chain unsaturated FAMEs that can be separated relatively easily (e.g., by distillation) along with the cyclohexadiene in the metathesis product. Production and utilization of such metathesis products is discussed further hereinbelow.

Small olefins utilized in the metathesis reactions of block 100, including, without limitation, ethylene, propylene, butylene, and isobutylene, can be obtained relatively cheaply from a petroleum refining process or can be obtained as by-products from catalytic vegetable oil cracking, without separation of the mixture. In embodiments, the olefins utilized for metathesis at stage 100 comprise alpha olefins having from two to five carbon atoms.

In applications, the fuel and chemical production process disclosed herein provides tailored fuel and chemical products in an economically desirable manner. In applications, at least a portion of the end product is a high-value by-product. The disclosed process permits modification and blending of fuel-stocks to provide a blended fuel tailored to meet desired fuel specifications.

Metathesis Catalyst. The metathesis reaction in metathesis stage 100 is carried out in the presence of an amount of metathesis catalyst effective to catalyze metathesis reaction(s) to a desired extent. The metathesis catalyst is any catalyst or catalyst system that catalyzes the metathesis reaction. Any known metathesis catalyst may be employed alone or in combination with one or more additional catalyst. Suitable metathesis catalysts include metal carbine catalysts based upon transition metals, including but not limited to ruthenium, chromium, rhenium, tungsten, molybdenum, and osmium. New catalysts conduct metathesis reactions of the unsaturated triglyceride oils with the olefins efficiently in the presence of the ester functional group.

Metathesis Methods. Specifications for a desired type of aviation fuel are satisfied by chemical compositions comprising alkanes (paraffins), isoalkanes (isoparaffins), cycloalkanes, and arylalkanes in specified proportions. To meet requirements for distillation range, viscosities, flash points, etc., the chain distributions for each fuel comprise a range of carbon chains appropriate for a fuel application, i.e., C9 to C14 for JP-8, as well as the distribution or blend of the various types of components. Automotive fuels have similar requirements, but some properties, such as cetane and flash point, can be extensively modified by additives. The key to achieving the appropriate blend and chain distribution for an aviation spec fuel via this disclosure is to utilize selected vegetable and algal oil precursors in an appropriate version of the metathesis reaction of the oil with selected olefin co-substrates at metathesis block 100 and the further integration with appropriate downstream conversion reactions at downstream processing block 200. Downstream processing stage 200 comprises production of both fuels at block 400 and chemical intermediates or products at block 500. Downstream processing 200 generally further comprises separation of metathesis products at 300 prior to production of fuel at 400 and production of chemical product or intermediate at 500, as indicated in the embodiment of FIG. 1. Substantially all of the carbons of the starting composition are efficiently utilized to provide high-value products, in certain applications of the disclosed method.

There are at least 12 ways to perform, at block 100, the metathesis reaction of an unsaturated fatty ester precursor. The preferred method depends on the type of lipid precursor available, desirable pre-processing, and the type of products desired. Methods of performing metathesis at metathesis stage 100 include, without limitation:
(1) cross-metathesis on FAME with ethylene;
(2) cross-metathesis on FAME with C2-C5 olefin mixture;
(3) cross-metathesis on glyceride with ethylene;
(4) cross-metathesis on glyceride with C2-C5 olefin mixture;
(5) partial cross-metathesis on FAME with ethylene;
(6) partial cross-metathesis on FAME with C2-C5 olefin mixture;
(7) partial cross-metathesis on glyceride with ethylene;
(8) partial cross-metathesis on glyceride with C2-C5 olefin mixture;
(9) self-metathesis on FAME;
(10) self-metathesis on glyceride;
(11) partial self-metathesis on FAME; and
(12) partial self-metathesis on glyceride.

The disclosed process integrates metathesis 100 comprising one or more of these methods of performing metathesis reaction with downstream processing 200 to provide one or more fuel and one or more chemical product. For example, in embodiments, metathesis at 100 comprises cross-metathesis of algal oil within a starting composition with olefin comprising or consisting essentially of ethylene (Method 1 in the list hereinabove). The starting composition is converted into metathesis product comprising cyclohexadiene from the polyunsaturated portion of the oil; one or more alkene; and chain-shortened esters comprising at least one carbon-carbon double bond. Downstream processing at 200 comprises, producing a chemical intermediate or product at 500. Producing a chemical intermediate or product 500 may comprise hydrocarbonylating cyclohexadiene of the metathesis product to create a dialdehyde. Producing a chemical intermediate or product at 500 may further comprise subsequently converting the dialdehyde to a bismethylamine, a dialcohol, or a dicarboxylic acid, all of which are suitable intermediates for polymer synthesis. Downstream processing 200 further comprises producing a fuel or fuel component from some of the metathesis products. Producing a fuel or fuel component 400 may comprise hydrotreating the chain-shortened esters and alkenes of the metathesis product over an isomerization catalyst to provide isoparaffin and paraffin components. The isoparaffin and paraffin components may be in a boiling range appropriate for jet fuels. Cyclohexadiene is also a suitable progenitor for the cycloparaffins and aromatics required for meeting the 25% alkylaromatic content of JP-8, and a portion of the cyclohexadiene of the metathesis product may be utilized at block 400 to produce one or more fuel component. As discussed in more detail hereinbelow, the remaining saturated esters are utilizable as superb high-cetane methyl biodiesel additives at block 400, or are converted at block 500 to low-melting triglycerides with a variety of uses in the food, cosmetic, and/or personnel thermal protection products.

Figure 2:
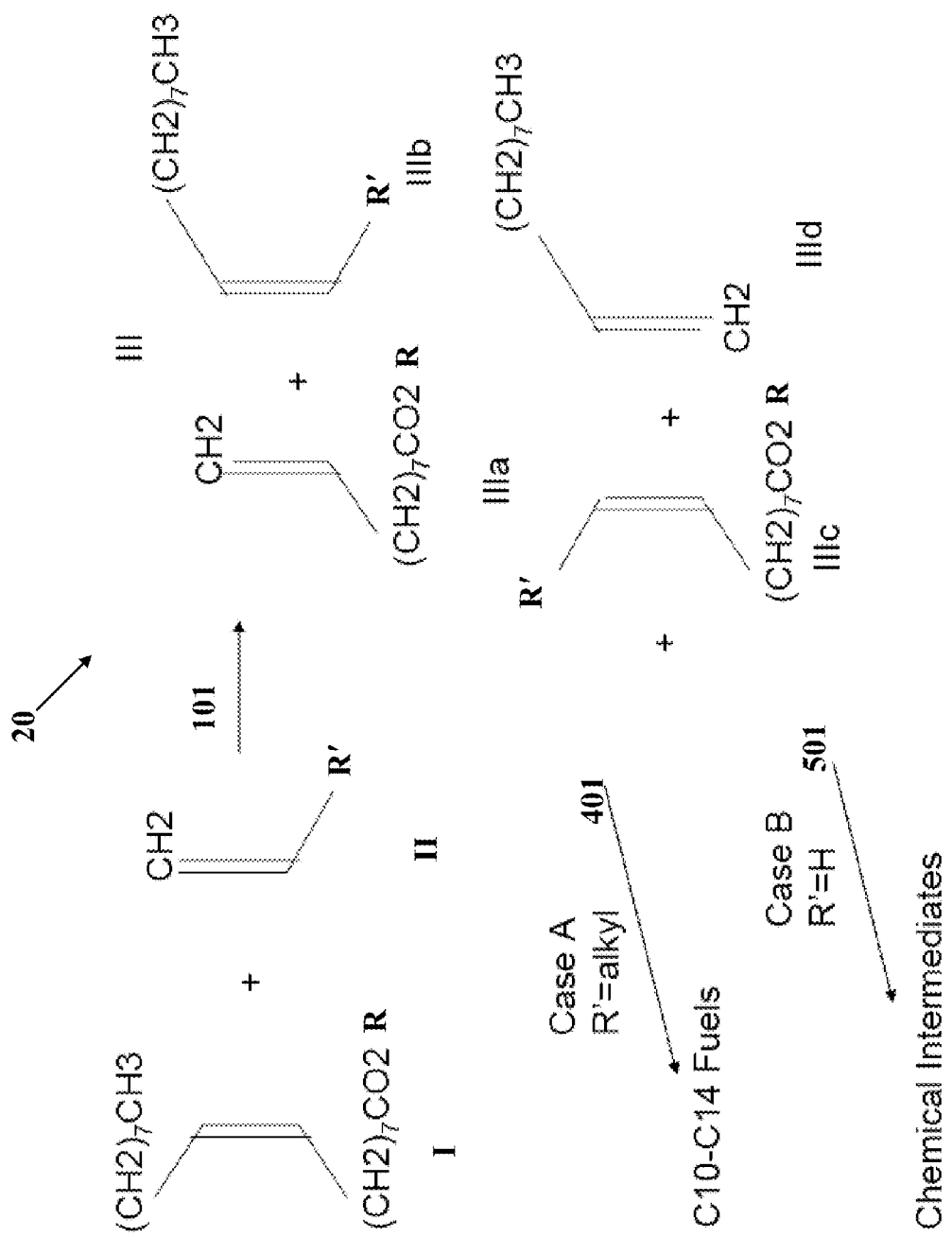
FIG. 2 is a schematic of an integrated fuel and chemical production process comprising cross-metathesis of oleate esters with alpha-olefins and subsequent downstream processing.

Processing Monounsaturated Oil. In embodiments, metathesis at block 100 comprises cross-metathesis of oleate esters with alpha-olefins or ethylene. FIG. 2 is a schematic of an integrated fuel and chemical production process 20 comprising cross-metathesis of oleate esters or triglycerides (I) with alpha-olefins or ethylene (II) and subsequent downstream processing. In this process, R is alkyl or triglyceryl. In embodiments, R is methyl. In embodiments, metathesis 101 reaction of monounsaturated (oleate) fatty esters I is carried out with an excess of olefin II. In Case A, in which R'=alkyl (e.g., methyl, ethyl, propyl, etc.), product III comprises four types of new unsaturated metathesis products, IIIa, IIIb, IIIc, and IIId, as illustrated in FIG. 2. While only cis-isomers are shown; trans-isomers will also be present. Using a C2 to C5 olefin mixture II, downstream processing 200 may comprise mildly hydrogenating the resulting C10 to C13 products with hydrogen over typical hydrogenation catalysts such as Pt and Pd to form mixtures of alkanes (C10 to C13) and fatty (C10 to C13) esters. In applications, downstream processing comprises production of fuel 401 by decarboxylating the carboxylate groups to the alkane over a Pd catalyst. Downstream processing may further comprise isomerizing over an isomerization catalyst to generate isoparaffins in the same range. Desired mixtures of products for certain fuels are selectively produced by varying the composition of the olefin feed II in the metathesis reaction 101 with the oleate ester I. However, the complex product mixture produced via Case A is generally not viable for production of chemicals other than azeleic acid, which may be produced via oxidation. Azelaic acid can more easily be provided directly from the starting fatty acid.

In applications, monounsaturated (oleate) fatty esters or triglyceride (I) are metathesized 101 with an excess of olefin II, where R' is hydrogen, i.e., the olefin is ethylene. In this case, Case B, where ethylene is the olefin feedstock, only two metathesis products III are produced (metathesis products IIIa and IIId). Downstream processing 200 may comprise producing chemical feedstock 501 by converting the omega-unsaturated ester (IIIa) to a C11 aldehyde ester and subsequently to valuable amino and hydroxyl esters as described by Lysenko et al. (U.S. Patent Application No. 2005/0154221 A1) and Abraham et al. (PCT Patent Application PCT/US2007/021931). The reaction with ethylene, Case B, provides, however, only 1-decene (IIId) as the alkene product, which does not meet fuel specifications. It is thus difficult to make both useful chemicals and useful fuels using monounsaturated substrates and methods.

Producing Chemicals and Fuels from Polyunsaturated Oils. For the production of both fuels and chemical or polymer intermediates or for production of multiple types or components of fuels, an alternative strategy is employed which uses di- and polyunsaturated precursors, such as those occurring in algal oils and many vegetable oils. Several vegetable oils comprise triglycerides of polyunsaturated as well as monounsaturated and saturated fatty acids. Suitable oils include, without limitation, oils from soybean, safflower, jatropha, sunflower, rapeseed, peanut, palm, cottonseed, and corn, which contain linoleate (18:2), and oils from linseed or flax, camelina, soybean, and palm, which contain linolenate (18:3). The precursors for the metathesis reaction can be simple alkyl esters produced in a preliminary transesterification step or the natural triglyceride forms or a whole algal oil comprising various forms of lipid ester. Consider the 12 variations discussed above for conducting the metathesis reaction with the di-unsaturated fatty ester, linoleate.

Figure 3:
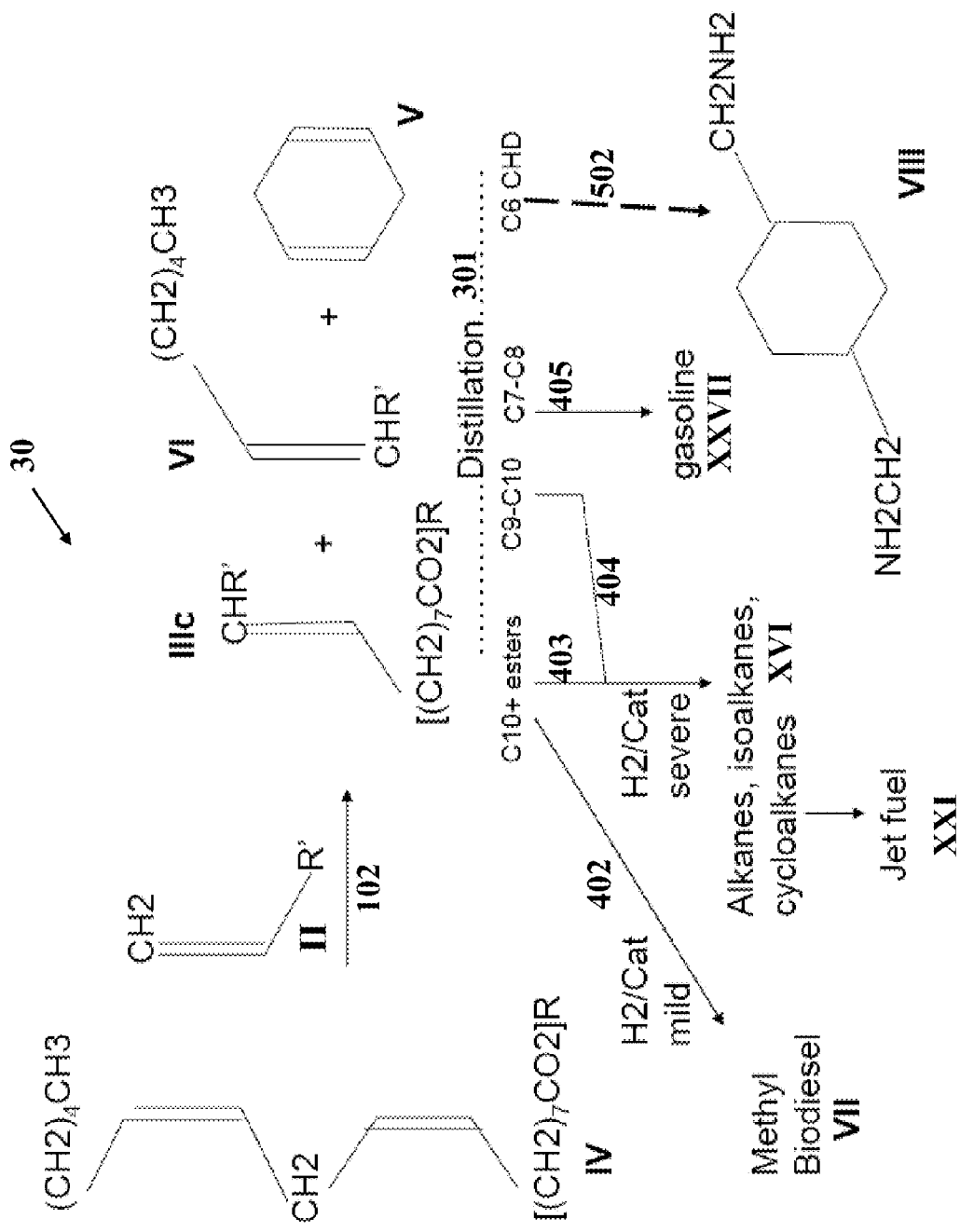
FIG. 3 is a schematic of an integrated fuel and chemical production process, according to an embodiment of the invention, comprising cross-metathesis of vegetable oil (linoleyl part of triglyceride) or methyl ester (linoleate methyl ester) and downstream processing.

The metathesis products of metathesis stage 100 for these 12 methods along with fuel and chemical products produced in downstream processing stage 200 are presented in Table 2. The implications of using the various metathesis methods for production of fuels and chemicals via downstream processing 200 are discussed in detail hereinbelow. FIG. 3 is a schematic of an integrated fuel and chemical production process 30, according to an embodiment of the invention, comprising cross-metathesis of vegetable oil or methyl ester and downstream processing. Exemplarily depicted is cross-metathesis 102 of the linoleyl part of the triglyceride oil or the linoleate methyl ester component IV and potential downstream processing of the cross-metathesis products. Cross metathesis 102 of the linoleyl part of the triglyceride oil or the linoleate methyl ester component IV and olefin II produces metathesis product comprising cyclohexadiene V, olefins VI, and higher molecular weight triglycerides or esters IIIC. Importantly, the cyclohexadiene product (V) is easily separated from the higher-molecular-weight unsaturated triglycerides (IIIC) and olefins (VI) by separation 301. Separation 301 may comprise distillation, crystallization, or another suitable method of separating the metathesis products.

TABLE 2

Potential Intermediate and Final Products from Metathesis of Linoleate (C18:2Δ9,12) Esters in Addition to the 1,4-Cyclohexadiene (CY)

| Metathesis Method | Ester | Olefin | Metathesis Intermediate Products | | Products of Downstream Processing | |
|---|---|---|---|---|---|---|
| | | | Olefin(s) | Ester(s) | Chemical(s) | Fuel(s) |
| 1 - Cross | FAME | C2 | C7:Δ1 | ME[1] C10:Δ9 | CY-der[2], C8 + C11-der | C10 BD[3] |
| 2 - Cross | FAME | C2 to C5 | C7:Δ1 to C10:Δ4 | ME C10:Δ9 to ME C13:Δ9 | CY-der | C10 to C13 BD<br>C9 to C13 jet<br>C6 to C8 gasoline |
| 3 - Cross | Glyceryl | C2 | C7:Δ1 | GE[4] C10:Δ9 | CY-der, C8 + C11-der | C10 BD |
| 4 - Cross | Glyceryl | C2 to C5 | C7:Δ1 to C10:Δ4 | GE C10:Δ9 to GE C13:Δ9 | CY-der | C10 to C13 BD<br>C9 to C13 jet<br>C6 to C8 gasoline |
| 5 - Partial Cross | FAME | C2 | C7:Δ1 + C10:2Δ1,4 | ME C10:Δ9 + ME C13:2Δ9,12 | CY-der | C10 + C13 BD<br>C9 to C13 jet |
| 6 - Partial Cross | FAME | C2 to C5 | C7:Δ1 + C10:2Δ1,4 to C10:Δ4 + C13:Δ4,7 | ME C10:Δ9 + ME C13:2Δ9,12 to ME C13:Δ9 + ME C16:2Δ9,12 | CY-der | C10 to C16 BD<br>C9 to C13 jet |
| 7 - Partial Cross | Glyceryl | C2 | C7:Δ1 + C10:2Δ1,4 | GE C10:Δ9 + GE C13:2Δ9,12 | CY-der | C10 + C13 BD<br>C9 to C13 jet |
| 8 - Partial Cross | Glyceryl | C2 to C5 | C7:Δ1 + C10:2Δ1,4 to C10:Δ4 + C13:Δ4,7 | GE C10:Δ9 + GE C13:2Δ9,12 to GE C13:Δ9 + GE C16:2Δ9,12 | CY-der | C10 to C16 BD<br>C9 to C13 jet |
| 9 - Self | FAME | | C12:Δ6 | Me C15:Δ9 + ME2 C18:Δ9 | CY-der azeleic | C15 BD<br>C9 to C15 jet |

TABLE 2-continued

Potential Intermediate and Final Products from Metathesis of Linoleate
(C18:2Δ9,12) Esters in Addition to the 1,4-Cyclohexadiene (CY)

| Metathesis Method | Ester | Olefin | Metathesis Intermediate Products | | Products of Downstream Processing | |
|---|---|---|---|---|---|---|
| | | | Olefin(s) | Ester(s) | Chemical(s) | Fuel(s) |
| 10 - Self | Glyceryl | | C12:Δ6 | GE C15:Δ9 + GE2 C18:Δ9 | CY-der azeleic | C15 BD C9 to C14 jet |
| 11 - Self Partial | FAME | | C12:Δ6 + C15:2Δ6,9 | Me C15:Δ9 + ME2 C18:Δ9 + ME2 C21:2Δ9,12 | CY-der azeleic | C15 BD C9 to C14 jet |
| 12 - Self Partial | Glyceryl | | C12:Δ6 + C15:2Δ6,9 | GE C15:Δ9 + GE2 C18:Δ9 + GE2 C21:2Δ9,12 | CY-der azeleic | C15 BD C9 to C12 jet |

[1]ME = Methyl Ester(s)
[2]der = Derivative(s);
[3]BD = Biodiesel;
[4]GE = Glyceryl Ester(s)

Utilizing Method (1) hereinabove, cross metathesis 102 of ethylene (olefin II with R' being hydrogen) with linoleate methyl ester (IV) gives 1,4-cyclohexadiene (V) plus 1-heptene (VI, R'=H) and methyl 9-decenoate IIIc (R'=H) which are separable by fractional distillation. As pure methyl linoleate (or pure triglyceride) may be expensive to obtain, the metathesis products from vegetable oil may comprise a mixture containing some 1-nonene (IIId) from metathesis of methyl oleate plus methyl stearate as well as the mentioned products from linoleate. Downstream processing 200 may comprise producing fuel blendstock 405 by hydroisomerizing the heptene to provide gasoline XXVII. However, hydrotreating these olefins and the decenoate to a jet or diesel fuel does not provide the required distribution of longer-chain (C11-C14) components. Downstream processing 200 may comprise producing fuel blendstock 402 comprising the separated methyl decenoate IIIc (R'=H) or its hydrogenation product methyl decanoate, which are high-cetane methyl diesel additives VII. The cyclohexadiene distillation cut comprising cyclohexadiene V is used to produce chemical feedstock 502. The cyclohexadiene cut contains mono-olefin impurities, so it may be reacted via hydrocyanation or hydrocarbonylation, to provide bis-adducts, such as VIII, which are more easily separated by distillation from the corresponding mono adducts from the mono-olefins and also the adduct from the unsaturated ester. Thereby caprylonitrile and caprinitrile or, alternatively, capryl aldehyde and capraldehyde are produced from C7 and C9 olefin, respectively, in downstream reactions. Thus the ethylene cross-metathesis provides good access to chemical feedstocks and also methyl diesel VII if desired. Impure 1-heptene can also be reacted in a second cross-metathesis with an olefin mixture to produce a range of larger olefins (C9-C13) useful for converting to jet fuel by hydrogenation and isomerization. Use of glyceryl esters in Method 3 (R=glyceryl) instead of methyl esters (R=methyl) is less desirable, as transesterification of IIIc (R'=H) is needed to obtain methyl biodiesel VII.

When the cross-metathesis reaction 102 is performed with a C2-C5 olefin mixture II (Method 2), a mixture of new olefins VI (R'=alkyl, H) is obtained in addition to the cyclohexadiene V and C10 to C13 unsaturated esters (IIIa, R'=alkyl, H). The new olefins VI comprise C7 to C10 olefins from the alkyl end of the linoleate IV, as well as C4-C8 olefins from reactions of the starting olefins II with themselves. Separation of the cyclohexadiene V from the resulting olefin mixture is far more difficult by distillation in this case because of the variety of olefins present. However, the impure C6 distillation cut can be further reacted as described hereinbelow with respect to FIG. 5 to obtain pure cyclohexane derivatives. In embodiments, the C2 to C5 cut is recycled. The C7-C8 cut can be isomerized at 405 to gasoline XXVII. At 404, 403, severe catalytic hydrogenation of the C9-C10 olefin cut and the C10 to C13 esters produces alkanes, isoalkanes, cycloalkanes XVI which can be hydroisomerized/decarboxylated to jet fuel XXI. The C10 to C13 esters are also mildly hydrogenated at 402 to a methyl C10-C13 biodiesel VII. This method produces both chemical intermediates and jet or biodiesel fuels with a good distribution of carbon chain lengths.

The use of glyceryl esters (Method 4) allows easier separation of the olefins from the esters in the metathesis products. This is not so important for linoleate but may be important in processing more highly unsaturated oils. In embodiment, glyceryl esters from the metathesis products of a starting composition comprising glyceryl functional groups R are transesterified to biodiesel VII or are used directly in conversion to jet fuel XXI.

Limiting the amount of olefin II or slowing the reaction results in partial conversions of the polyunsaturated chains to produce dienes with a wider variety of chain lengths, at the expense of cyclohexadiene. Using Method 5 and especially Method 6 allows for formation of better distributions of components in both methyl biodiesel and jet fuel products. However, formation of C14 to C16 components from the C2 to C5 olefin feed is not useful for jet fuel and is even high for diesel, but the C14-C16 esters are useful for biodiesel. Thus the partial metathesis is used for highly polyunsaturated feeds rather than linoleate, because the distribution of chain lengths in the product olefins and esters will extend to the range required for jet fuel and diesel (see discussion hereinbelow).

Utilization of glyceryl esters with partial conversion (Methods 7 and 8) gives similar products, but separation of the esters from the olefins is facilitated, owing to their very high molecular weights. This is useful for obtaining jet and biodiesel (after transesterification) in desirable ranges.

The self-metathesis of methyl linoleate (Method 9) gives only the decene in addition to the cyclohexadiene and ester products. The 6-dodecene and the C18 diester are of limited value, but the C15 ester is easily obtained by distillation and used as biodiesel or hydrotreated to jet. Both unsaturated esters can be oxidized to azeleic acid.

Self-metathesis of the glyceryl linoleate (Method 10) likewise gives products of limited usefulness. Partial self-metathesis (Methods 11 and 12) gives a wider variety of olefins and esters, but unfortunately, the products are larger and less useful for production of spec fuels.

Cyclohexadiene is formed in all of the metathesis reactions of linoleate esters. Less cyclohexadiene is formed from the partial reactions, since the central portion of the linoleate (C10-C12) is only partially converted to cyclohexadiene and partially to diene intermediates containing the three extra carbons. Thus, in embodiments, to maximize formation of chemical intermediates, the metathesis reaction at stage 100 is run as far to completion as possible. In other embodiments, partial conversion by metathesis at stage 100 is utilized to maximize jet fuel production.

Thus to facilitate the production of fuels and chemicals via the method of this disclosure, polyunsaturated esters IV are cross-metathesized 102 with small olefins II as in the embodiment of FIG. 3. In embodiments, the separated olefin VI and unsaturated esters IIIc are hydrotreated to alkanes, isoalkane, and cycloalkanes XVI. Thus by using the polyunsaturated precursors and an effective separation 301 between the cyclohexadiene V and the other metathesis products VI, IIIc, one can obtain both useful chemicals and fuels.

Figure 4:
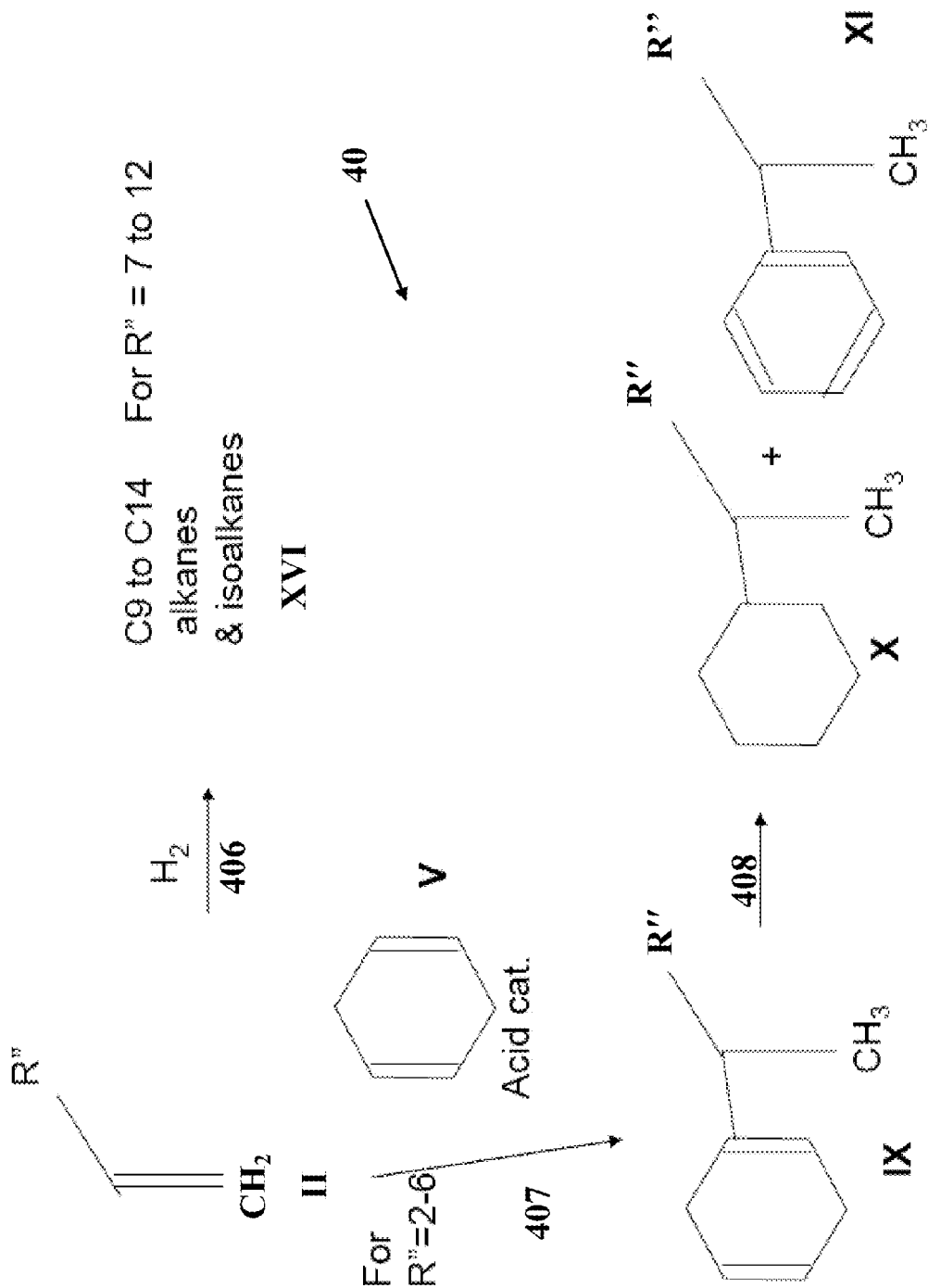
FIG. 4 is a schematic of a downstream processing method, according to an embodiment of the invention, for synthesizing cycloparaffins and alkylaromatics via acid-catalyzed reaction of cyclohexadiene with alpha-olefins.

The metathesis product comprises cyclohexadiene V. Cyclohexadiene is the key intermediate for downstream processing of metathesis products to produce fuel blendstock components, chemical feedstocks, or both according to the integrated method of this disclosure. In embodiments of the method, cyclohexadiene is used to produce valuable difunctional monomers for synthesis of polymers. In embodiments of the fuel and chemical production method, cyclohexadiene is utilized for synthesis of cycloparaffins and/or aryl paraffins suitable for the production of JP-8 fuel. FIG. 4 is a schematic of a downstream processing method 40, according to an embodiment of the invention, for synthesizing cycloparaffins and alkylaromatics via acid-catalyzed reaction of cyclohexadiene with alpha-olefins. In the embodiment of FIG. 4, cycloparaffins and alkylaromatics are synthesized 407 via acid-catalyzed reaction of cyclohexadiene V with alpha-olefins II. In embodiments, R" is an alkyl group, selected from C2-C6 alkyl groups. Smaller alpha-olefin products (R"=C2 to C6), which may be obtained from metathesis at 100, are reacted with cyclohexadiene V in the presence of a strong acid catalyst to give alkylation products IX. The strong acid catalyst may be $H_2SO_4$ or solid superacid catalyst. The alpha-olefin II attaches at the second carbon of cyclohexadiene V to produce the branched alkyl-substituted cyclohexadiene IX. This product IX is disproportionated at 408 to a mixture of cycloparaffins X and alkylaromatics XI with chain lengths appropriate for jet fuel blends. As discussed previously with regard to FIG. 3, the larger olefins (R"=C7 to C12) are hydrotreated at 406 to give alkanes and isoalkanes XVI suitable for jet fuels XXI.

Figure 5:
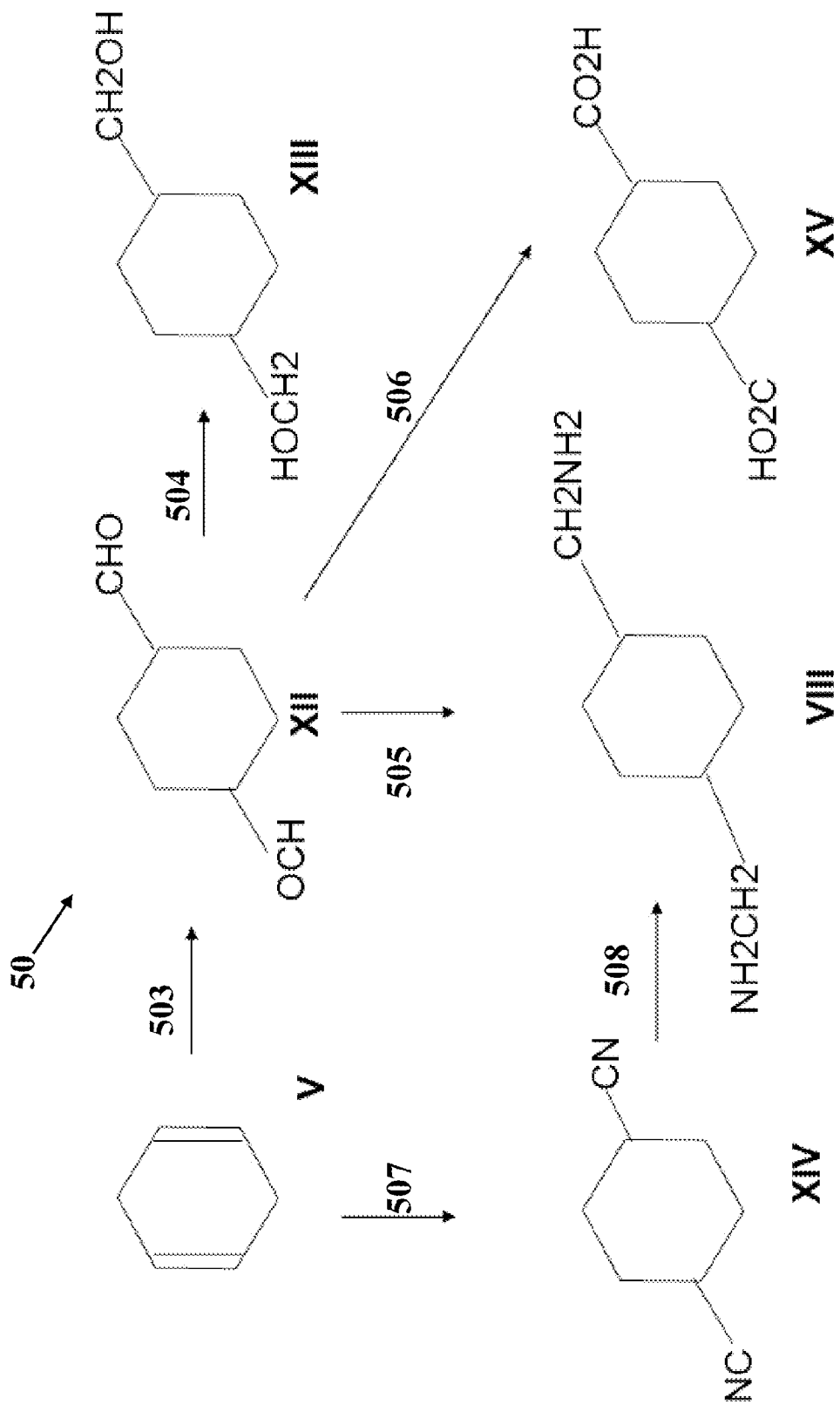
FIG. 5 is a schematic of a downstream processing method, according to an embodiment of the invention, for synthesizing disubstituted cyclohexane intermediates suitable for synthesis of polymers.

Producing chemical feedstock 500 may comprise synthesis of monomers. FIG. 5 is a schematic of a downstream processing method 50, according to an embodiment of the invention, for synthesizing disubstituted cyclohexane intermediates suitable for synthesis of polymers. As shown schematically in FIG. 5, for the synthesis of monomers, 1,4-cyclohexadiene V is converted at 503 to cyclohexanedicarboxaldehyde XII by hydrocarbonylation with carbon monoxide and hydrogen. In applications, the cyclohexanedicarboxaldehyde XII is subsequently converted at 504 to cyclohexanedimethanol XIII by hydrogenation, to cyclohexanebismethylamine VIII by reductive amination at 505, and/or to cyclohexanedicarboxlic acid XV by oxidation at 506. Bifunctional monomers, XIII, VIII, and XV are suitable for the synthesis of polyesters, polyurethanes, polyamides, and/or polyureas. In applications, the 1,4-cyclohexadiene metathesis product V is converted at 507 to the cyclohexanedinitrile XIV by hydrocyanation and, subsequently, to the bisamine VIII by hydrogenation of the nitrile groups at step 508.

Linolenate triglyceride in oils also provides 1,4-cyclohexadiene V from the central portion (C10 to C15). Complete reaction of docosahexaeneoate from algal oil gives 2.5 moles of 1,4-cyclohexadiene from the polyunsaturated chain, representing 15 of the 22 carbons. Another component of algal oil is eicosapentaenoate, which gives 2 moles of cyclohexadiene, representing 12 of the 20 carbons.

Other variations of the disclosed method produce other specific fuel components. In embodiments, aromatics are introduced as the R group by using styrene or, perhaps, pyrolyzed waste polystyrene in the cross-metathesis. This provides C16 alkylbenzene, i.e., decylbenzene. Alternatively, the C10-C13 olefins are combined with benzene, toluene, or xylene using an acid catalyst to produce alkylaromatics, useful for surfactant synthesis or for jet fuels.

Specialty fuels require a mixture of structural isomers of each of the chain lengths. These isomer mixtures are readily formed on an isomerization catalyst with minimal cracking if the feedstock is an alkene. Thus, in embodiments, the alkene products (IIIb, IIId, VI, etc.) from the metathesis reactions in metathesis stage 100 described above are passed over an isomerization catalyst in downstream processing 200 prior to hydrogenation to a final product.

Starting Composition Comprising Polyunsaturated Algal Oil

Figure 6:
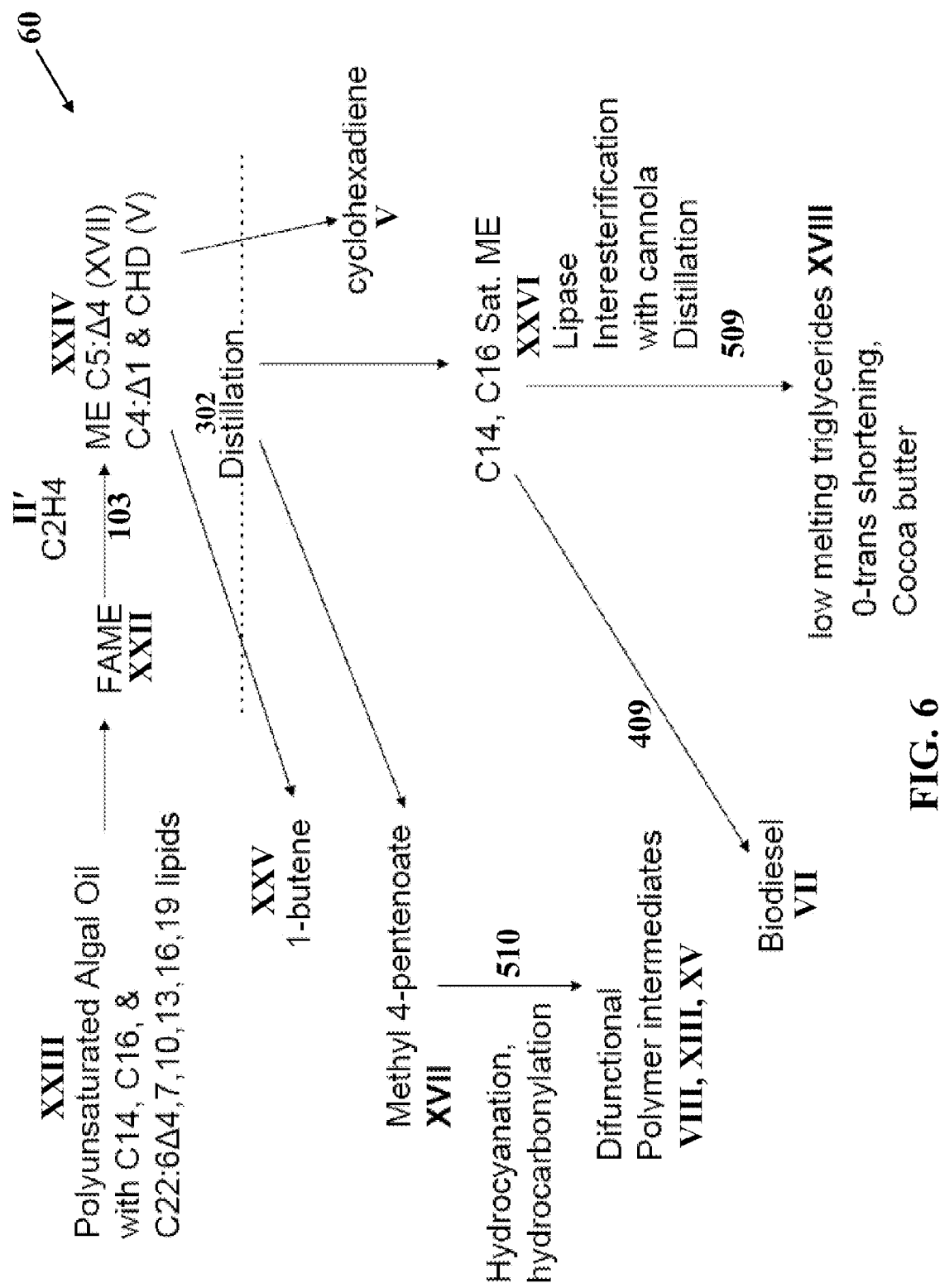
FIG. 6 is a schematic of an integrated fuel and chemical production process, according to an embodiment of the invention, comprising complete metathesis of algal oil and downstream processing, wherein complete metathesis comprises substantially complete reaction of the polyunsaturated chains of the algal oil.

Substantially Complete Reaction of Polyunsaturated Chains. A particularly desirable embodiment of the fuel and chemical production method of this disclosure is the integration of metathesis reactions at metathesis stage 100 with downstream processing 200, wherein the starting material comprising algal oil(s). FIG. 6 is a schematic of an integrated fuel and chemical production process 60, according to an embodiment of the invention, comprising complete metathesis of algal oil and downstream processing, wherein complete metathesis comprises substantially complete reaction of the polyunsaturated chains of the algal oil. Integrated processing scheme 60 comprises metathesis 103 of algal FAME XXII with complete reaction of the polyunsaturated chains of the algal FAME XXII with ethylene II' (Method 1). The FAME XXII may be produce via pretreatment of a starting composition comprising polyunsaturated algal oil with C14, C16, and C22:6Δ47, 10, 13, 16, 19 lipids XXIII as discussed hereinabove. A typical algal FAME composition contains about equal amounts of ME C14, ME C16, and ME C22:6. When the cross-metathesis reaction 103 is taken to completion, as illustrated in FIG. 6, the products XXIV can easily be separated by simple distillation 302, owing to the diverse boiling points thereof. Cross metathesis in this manner produces large amounts of cyclohexadiene V and smaller amounts of 1-butene XXV. The 1-butene XXV is suitable as a coreactant in other metathesis reactions and/or in other chemical processing. The cyclohexadiene V is converted to difunctional intermediates VIII, XIII, and/or XV for polymers as described hereinabove with respect to FIG. 5 or to cycloparaffins X and/or XI as described hereinabove with respect to FIG. 4.

The ester components of the metathesis products XXIV comprise saturated C14 to C18 FAME XXVI originally present in the starting composition plus the unsaturated ester formed in the metathesis 103 of the polyunsaturated FAME XXII. The unsaturated ester comprises 4-pentenoate XVII and/or 5-hexenoate from the C22:6 and/or C20:5 acyl groups, respectively.

Saturated FAMEs XXVI may be utilized at 409 for biodiesel VII. In embodiments, the saturated FAMEs XXVI are obtained for reactions of the interesterification type that yield valuable products. Interesterification 509 of the saturated ester product XXVI with triolein (or canola oil) exchanges the C14-C18 saturated acids for two of the oleyl groups in the triglyceride producing a low-melting disaturated acyl monooleylglyceride XVIII, similar to cocoa butter, margarine, and shortening. The reaction 509 is catalyzed by a lipase enzyme, such as lipozyme RM IM from *Rhizomucor miehei*. The cis configuration of oleyl is conserved since no hydrogenation is performed, and metathesis 103 was conducted in an earlier step. Thus no trans-configurations are generated. The interesterification products are separated by short path distillation, providing methyl oleate and disaturated acyl monooleyl glyceride XVIII. These have melting points of less than 100° F. These products are also valuable for the manufacture of protective gels that absorb large amounts of heat (because of melting enthalpy) and can, therefore, keep body temperature in normal ranges during exposure to excessive conditions. For example, a heat absorbing material may be produced from the low-melting metathesis-modified triglyceride. The heat absorbing material may be used to create a panel that, when in contact with human skin, absorbs internal or external heat, maintaining the skin at normal skin temperature.

Besides the important value of the cyclohexadiene V and saturated ester product XXVI as a chemical intermediate, the unsaturated ester products, e.g. XVII, and olefin products, e.g. XXV, are useful for production of fuel and chemical products. Methyl 4-pentenoate XVII can be converted at 510 to amino ester intermediates (e.g., VIII, XIII, and/or XV) via hydrocyanation and hydrogenation. The amino ester intermediates may then be polymerized to desirable polymers, for example, to nylon-6. The olefin cross-metathesis products (e.g., XXV) obtained from the omega end of the fatty acids are valuable for providing several components of jet fuels. For example 1-butene XXV from the omega-3 fatty acids is reacted with cyclohexadiene V in the alkylation reaction of FIG. 4 to provide cycloparaffins X, XI. Alternatively or additionally, the 1-butene XXV can be oligomerized to a series of alkenes (dimers, trimers, tetramers) from which isoparaffins for jet fuel XXI are produced.

Utilizing an olefin mixture with algal FAME (Method 2) results in large amounts of cyclohexadiene V plus a mixture of short-chain unsaturated esters and olefins. If the reactant olefins comprise C7:Δ1 to C10:Δ1 and also C12:Δ6, then the resulting unsaturated esters comprise ME C10 to C13 and the product olefins C9 to C12, appropriate for hydrotreating to jet fuels. It should be recognized that the required C7 to C10 feed can be obtained from the products of vegetable oil metathesis (Table 2).

Figure 7:
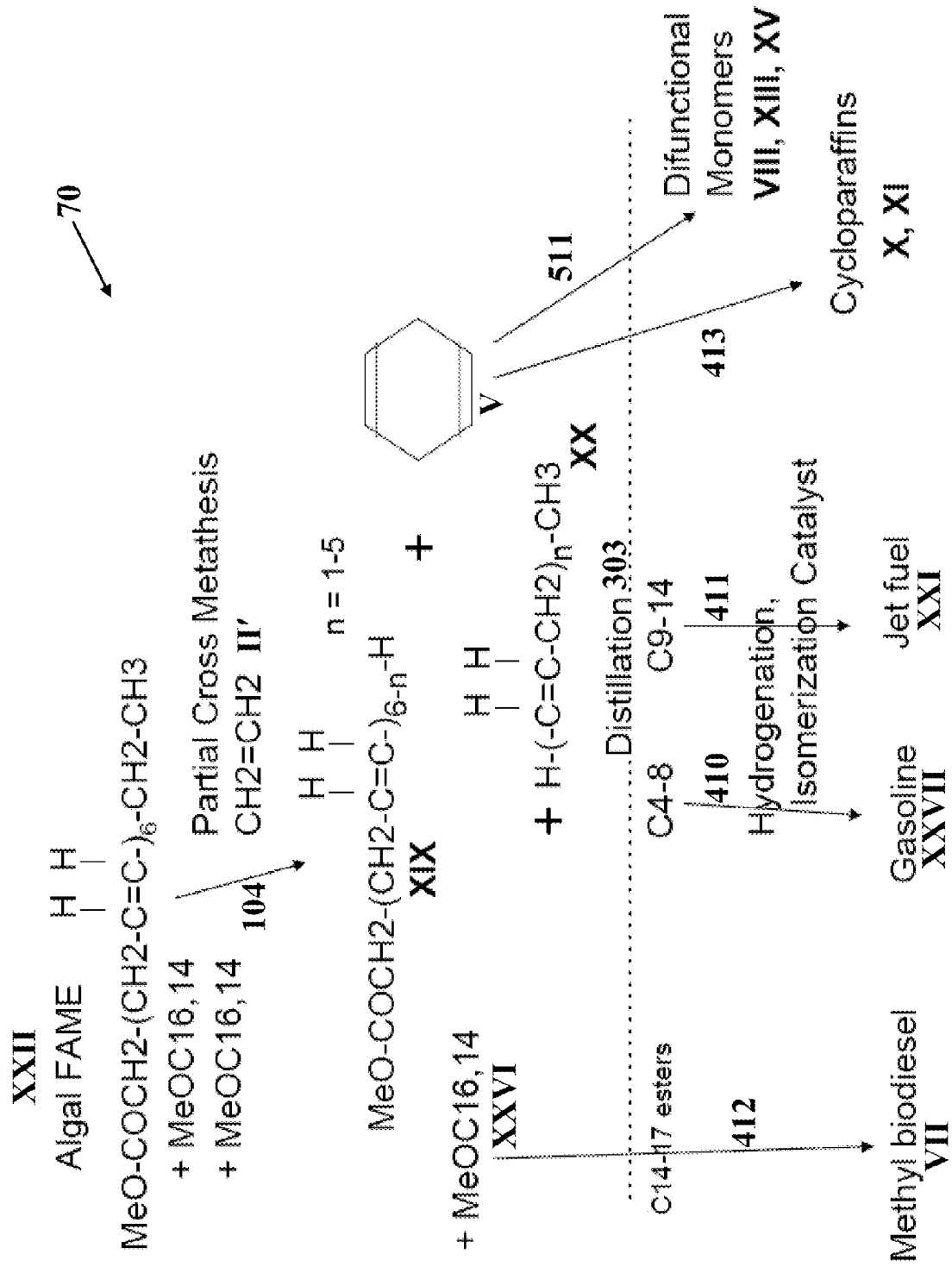
FIG. 7 is a schematic of an integrated fuel and chemical production process, according to an embodiment of the invention, comprising partial metathesis of algal and/or vegetable fatty acid methyl ester(s) or "FAME," and downstream processing of metathesis products; partial metathesis comprises limited (partial) reaction of the polyunsaturated chains of the algal FAME and/or vegetable FAME to provide distributions of chain lengths in the resulting products.

Partial Reaction of Polyunsaturated Chains. Especially useful for the production of JP-8 fuels as well as bifunctional polymer intermediates is a variation of the metathesis reaction of the algal FAME with ethylene, wherein the metathesis reaction is only partially completed (Method 5). FIG. 7 is a schematic of an integrated fuel and chemical production process 70, according to an embodiment of the invention, comprising partial metathesis 104 of algal and/or vegetable fatty acid methyl ester(s) or "FAME," and downstream processing of metathesis products; partial metathesis comprises limited (partial) reaction of the polyunsaturated chains of the algal FAME and/or vegetable FAME to provide distributions of chain lengths in the resulting products. Starting composition comprising algal FAME XXII is partial cross-metathesized at 104 with ethylene II' to produce metathesis products comprising cyclohexadiene V, unsaturated ester products XIX, saturated ester components XXVI, and olefin products XX.

The metathesis reaction 104 can be controlled by using low temperatures, short reaction times, small amounts of catalyst, and/or a small amount of olefin coreactant II'. In this embodiment, partial cross metathesis at step 104 of the polyunsaturated chain of FAME XXII with ethylene II' provides a mixture of products, where one or more of the double bonds has reacted. Thus the product still contains some cyclohexadiene V for chemical synthesis, but the olefin portion XX and unsaturated ester portions XIX now contain a distribution of chain lengths and multi-unsaturation, as indicated in FIG. 7. This is a result of cleavage at various points (double bonds) in the C22 chain. Distillation 303 or other suitable separation method is used to separate cyclohexadiene V, olefin portion XX, and unsaturated ester portion XIX. Hydrogenation and isomerization of this product mixture provides a better distribution of chain lengths in the product fuel(s). The C4-C8 components of the unsaturated olefin and unsaturated ester portions XX and XIX respectively may be hydrogenated and isomerized at 410 to gasoline XXVII. The C9-C14 components of the unsaturated ester and olefin portions XIX and XX respectively may be hydrogenated and isomerized at 411 to provide jet fuel XXI. The C14-C17 esters, including saturated C16, 14 esters, may be utilized at 412 for biodiesel VII. The cyclohexadiene V is converted at 511 to difunctional intermediates VIII, XIII, and/or XV for polymer synthesis as described hereinabove with respect to FIG. 5 and/or to cycloparaffins X and/or XI at 413 as described hereinabove with respect to FIG. 4.

EXAMPLES

Partial cross-metathesis of safflower oil with ethylene (1:10 molar ratio) was conducted in a stirred autoclave at 25° C. with a commercially available metathesis catalyst (Grubbs second-generation catalyst). Safflower oil contains mostly oleic (18:1) and linoleic acid (18:2) and small amounts of saturated acids. Olefin products were separated from the shortened-chain glyceryl esters by distillation. These olefin products included 1,4-cyclohexadiene, 1-heptene, 1-decene, 6-dodecene, and 6-pentadecene and small amounts of 1,4-decadiene, 1,4-tridecadiene, 9-octadecene, 6,9-octadecadiene, and 9,12-uncosadiene and very small amounts of other hydrocarbons. Several of the products indicate incomplete reaction with the ethylene, which is beneficial for fuel production.

The olefins are distilled such that a "kerosene range" cut (C10 to C15) is obtained, which is then hydrotreated with a catalyst that partially isomerizes and hydrogenates the olefins to produce a mixture of paraffins and isoparaffins (C10 to C15). Such catalyst comprises a Group VIII metal (Pd, Pt, Ni) on a zeolitic or acidic support (H-beta, ZSM22, ZSM23, SAPO-11). The high selectivity of this process results in high conversion to a C10 to C15 product with a boiling range appropriate for jet fuel (205°-300° C.).

Cyclohexadiene is recovered from the distillation and converted either to alkyl cyclohexanes (cycloparaffins) for addition to the jet fuels or is hydrocarbonylated and hydrocyanylated to form polymer precursors. The higher distillation cut is cycled to subsequent oil metathesis reactions.

The separated glyceryl ester portion of the product from safflower oil includes some oligomeric material resulting from reversion or self-metathesis. The glyceryl residue is treated with methanol and a basic catalyst to form the methyl esters of the altered chain fatty acids. This product comprises methyl esters of 9-decenoic acid (mainly), 9,12-tridecenoic acid, 9-pentadecenoic acid, and 9-octadecendioic acid and contains a small amount of unreacted oleic, linoleic, and saturated acids. This product is hydrotreated with a Pd catalyst on a zeolitic support to produce C9 to C18 paraffins and isoparaffins. Processing of the acid portion of the triglyceride product to jet fuel blendstock can also be accomplished by hydrotreating the fatty acid mixture obtained by basic hydrolysis or even by hydrotreating directly the shortened-chain triglycerides.

The self-metathesis reaction of flax oil with the Grubbs second-generation catalyst at 40° C. gives a different set of products. The glyceryl esters form a cross-linked gel. The olefins separated by decantation from the gel comprise the following set: 3-hexene, 1,4-cyclohexadiene, 6-dodecene, 6-pentadecene, and 9-octadecene. Only very small amounts of partially reacted chains were present from the reaction at this temperature. The glyceryl esters were essentially 9-decenoic and 9-octadecenoic esters.

Additional reactions include Diels-Alder addition (2+4 cycloaddition) of butadiene or cyclopentadiene to the alkenes and cyclohexadiene to form C14 to C17 alkylcyclohexenes and bicyclic alkenes for synthesis of high-energy fuels, similar to RJ-4, RJ-5, and JP-10.

While preferred embodiments of the invention have been shown and described, modifications thereof can be made by one skilled in the art without departing from the spirit and teachings of the disclosure. The embodiments described herein are exemplary only and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc., should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus the claims are a further description and are an addition to the preferred embodiments of the present invention. The discussion of a reference is not an admission that it is prior art to the present invention, especially any reference that may have a publication date after the priority date of this application. The disclosures of all patents, patent applications, and publications cited herein are hereby incorporated by reference, to the extent they provide exemplary, procedural, or other details supplementary to those set forth herein.

What is claimed is:

1. A process comprising:
   (a) providing an algal oil comprising polyunsaturated glycerides, saturated and unsaturated $C_{14}$-$C_{18}$ fatty acids;
   (b) self-metathesizing or crossmetathesizing the algal oil with at least one short chain olefin reactant in the presence of an amount of a metathesis catalyst effective to form metathesis products comprising (i) one or more olefin compounds determined by the selection of the at least one short-chain olefin reactant, (ii) an unsaturated carboxylic acid or ester with five or more carbons and unsaturation at C4 and (iii) a saturated ester fraction; and
   (c) processing the saturated ester fraction via selective lipase reaction.

2. The method of claim 1 wherein selective lipase reaction comprises lipase-catalyzed interesterification of an acyl portion of the saturated ester fraction with canola oil, and wherein interesterification produces a low-melting point modified triglyceride comprising saturated and monounsaturated fatty acids and having a melting point in the range of from about 90° F. to about 100° F.

3. The method of claim 2 further comprising producing a heat-absorbing material from the low-melting point modified triglyceride.

4. The method of claim 3 wherein the heat-absorbing material comprises a panel that is capable of absorbing external or internal heat, when in close contact with human skin, maintaining the skin at normal skin temperature.

5. The method of claim 1 wherein the short chain olefin reaction is ethylene.

6. The method of claim 1 wherein the polyunsaturated glycerides comprise C22:6Δ4, 7, 10, 13, 16, 19 fatty acids or C20:5Δ5, 8, 11, 14 and 17 fatty acids.

* * * * *